United States Patent [19]
Bachynsky

[11] Patent Number: 5,267,963
[45] Date of Patent: Dec. 7, 1993

[54] MEDICATION INJECTION DEVICE

[76] Inventor: Nicholas Bachynsky, 47424-079, FMC, P.O. Box 99001, Carville, La. 70721

[21] Appl. No.: 934,014

[22] Filed: Aug. 21, 1992

[51] Int. Cl.$^5$ .......................... A61F 5/00; A61M 5/00
[52] U.S. Cl. ...................... 604/134; 604/157
[58] Field of Search ............... 604/136, 137, 134, 173, 604/156, 157, 187

[56] References Cited

U.S. PATENT DOCUMENTS

| | | | |
|---|---|---|---|
| 3,515,127 | 6/1970 | Reymond . | |
| 3,656,472 | 4/1972 | Ben Moura . | |
| 3,702,608 | 11/1972 | Tibbs | 604/136 |
| 3,797,489 | 3/1974 | Sarnoff | 604/136 |
| 3,941,130 | 3/1976 | Tibbs . | |
| 4,150,669 | 4/1979 | Latorre . | |
| 4,188,950 | 2/1980 | Wardlaw . | |
| 4,261,358 | 4/1981 | Vargas et al. . | |
| 4,333,459 | 6/1982 | Becker | 604/136 |
| 4,512,767 | 4/1985 | Denance | 604/137 |
| 4,723,937 | 2/1988 | Sarnoff et al. | 604/136 |
| 4,787,891 | 11/1988 | Levin et al. | 604/136 |
| 4,850,973 | 7/1989 | Jordan et al. | 604/136 |
| 5,037,396 | 8/1991 | Streeter . | |
| 5,137,516 | 8/1992 | Rand et al. | 604/136 |
| 5,167,632 | 12/1992 | Eid et al. | 604/136 |

OTHER PUBLICATIONS

*Organic causes of male sexual dysfunction; The evaluation and treatment of impotence;* E. David Crawford, MD., and Frank Mayer, Md; *Modern Medicine,* vol. 59, pp. 63–82, Sep., 1991.

*Better Prognosis; Research on Impotence Upsets Idea that it is Usually Psychological;* David Stipp; *The Wall Street Journal,* Tuesday, Apr. 14, 1987.

*A look at alternaitves; U.S. News & World Report,* p. 67, Aug. 24, 1992.

*Primary Examiner*—Paul J. Hirsch
*Attorney, Agent, or Firm*—Pravel, Hewitt, Kimball & Krieger

[57] ABSTRACT

This invention relates to an automatic injection device which, upon activation by the user, automatically extends a syringe with needle, delivers medication through the needle, and retracts the needle, thus keeping the needle hidden from view.

27 Claims, 2 Drawing Sheets

MEDICATION INJECTION DEVICE

BACKGROUND OF THE INVENTION

1. Field of the Invention

This invention relates to a medication injection device which, upon being activated by the user, delivers medication from a syringe with needle to the user with the needle being in a retracted, hidden position at all times except when actual injection occurs. More particularly, this device permits treatment of appropriate cases of male erectile dysfunction by accurate placement and introduction of substances into the erectile bodies (corpora cavernosa) of the penis.

2. Description of the Related Art

It is well known that many persons are apprehensive of receiving an injection from a hypodermic needle. This situation is worsened for those who must administer their own injections, such as diabetic patients and others who regularly require medication or who require that medication be administered in private or in emergency situations, such as acute allergies to insect bites (anaphylaxis), hypoglycemic reactions, etc. This apprehension is particularly acute in the treatment of male erectile dysfunction with direct injection of medication into the penis.

While the invention is intended to be used in conjunction with the administration of medicine of any physical form to various parts of the body and to various tissue depths, it is particularly applicable for use in the treatment of erectile dysfunction.

Defined simply, erectile dysfunction occurs when a male is unable to maintain adequate penile rigidity necessary to initiate, sustain and successfully consummate the act of coitus. It denotes organic impotence.

This condition can be a psychologically devastating therapeutic problem. It has been estimated to effect 50% of all diabetic men and up to 9% of younger men in apparent good health. Varying degrees of erectile dysfunction caused by age, drug use, arteriosclerosis, trauma, hormone disorders and surgical procedures have also been observed. Diminished male erectile response is the limiting factor in sexual relationships. The fear of erectile failure has been reported as one of the primary reasons for decreased libido in older males.

The penile erection mechanism of the normal male is a complex interaction of hormones, neurotransmitters and blood vessels. An erection begins when paired penile arteries dilate in response to neurotransmitters relaxing the smooth muscle walls of the arteries. An increased incoming blood flow engorges the chambers of the penis (corpora cavernosa) where it is trapped. The tough and fibrous encasing tunica albuginea is stretched by tumescence and compresses perforating veins which drain the blood filled chambers. Venous drainage is impeded and further penile rigidity ensues. In organic impotent males, this vascular-erection mechanism is substantially impaired, not activated or not intact.

Self-injection of vasoactive pharmacotherapeutic agents directly into the penis for treatment of erectile dysfunction is known. Intracavernous papaverine, phentolamine and prostaglandin $E_1$ frequently are used individually or in synergistic mixtures to replace the absent neurotransmitter mediated vascular dilatation and subsequent physiologic erection. Nitric oxide or a natural neuro-transmitter-hormone, vasoactive intestinal peptide, may be the future vasoactive agents of choice.

While clinical success with intra-cavernous pharmacotherapy exceeds 75%, many patients do not initiate or abandon self-injection therapy once it has been tried. The most common reason self-injection is not used is a universal phobia of introducing a needle into one's penis. Other reasons include on older patient's ineptitude, manual tremors and loss of dexterity necessary to locate injection site; physical handicaps of blindness, loss of limb and abdominal obesity; transportation inconvenience; prolonged syringe needle-vial drawing techniques; lack of spontaneity during love making; objections from sexual partner; and lack of self-injection confidence, plus the natural apprehensions that professional assistance is required to avoid hemorrhage or priapism.

Various types of syringes have been developed for injecting drugs into the penis or for self-administration of drugs into other parts of the body. These devices, which have proved ineffective for various reasons, include the one shown in U.S. Pat. No. 4,150,669 to Latorre. A dual hypodermic needle syringe for injecting fluids into the penis is shown, which has two parallel, interconnected barrels connected to needles extending from the barrels. This device has the disadvantage that the syringe needles must be manually introduced into the penis and manual depression of the plunger(s) is required to inject the medicinal fluid from the syringe and needle into the penis.

Various forms of spring-equipped syringe holders and actuators are known, such as the ones shown in U.S. Pat. Nos. 3,941,130 (Tibbs), 4,261,358 (Vargas et al.) and 4,188,950 (Wardlaw). However, these devices do not utilize a mechanism which allows for automatic insertion of the needle, injection of the fluid, and retraction of the needle provided in a compact, discrete device.

Thus, there exists the need for an automatic injection device which allows easy and accurate self-injection of medication. This need is particularly acute in the self-injection of medication into one's penis where there is the additional need of keeping the needle hidden from view to eliminate needless anxiety.

SUMMARY OF THE INVENTION

The invention relates to an automatic injection device, which upon activation by the user, automatically introduces a needle into an individual, injects the medication contained in the syringe and then retracts the needle from the individual. While the present invention relates to injection into any body part and to any depth, i.e., intradermal, subcutaneous, or intramuscular, the preferred embodiment relates to direct, automatic injection of medication into the penis for treatment of male erectile dysfunction.

The automatic injection device has a housing with a sliding cam mechanism which is powered by an extended spring and activated by a trigger mechanism. The housing has an integral barrel section located perpendicular to the path of the sliding cam mechanism which contains a syringe with needle. Upon activation, one surface of the sliding cam mechanism contacts the syringe, pushing the syringe from its initial position to an extended position such that the needle is inserted into the individual. A second surface of the sliding cam mechanism pushes the syringe plunger for administering fluid contained in the syringe into the individual.

The needle is then automatically retracted within the barrel such that the needle remains hidden from sight.

The present invention provides an automatic injection device which will inject medication with an unseen needle, thus overcoming an individual's fear of needles while providing convenience and the proper dosage.

The present invention also provides a useful device which makes self-injection of medication into the penis for cases of erectile dysfunction a relatively simply procedure. The device allows easy and correct placement with a hidden needle that automatically penetrates, injects medication and retracts.

The device is also compact, discrete, and easily disposable since the needle is retracted to a position that eliminates the problem of accidental "needle stick" of another.

BRIEF DESCRIPTION OF THE DRAWINGS

A better understanding of the invention can be obtained when the detailed description of exemplary embodiments set forth below is considered in conjunction with the attached drawings, in which.

DETAILED DESCRIPTION OF EXEMPLARY EMBODIMENTS

Figure 1A:
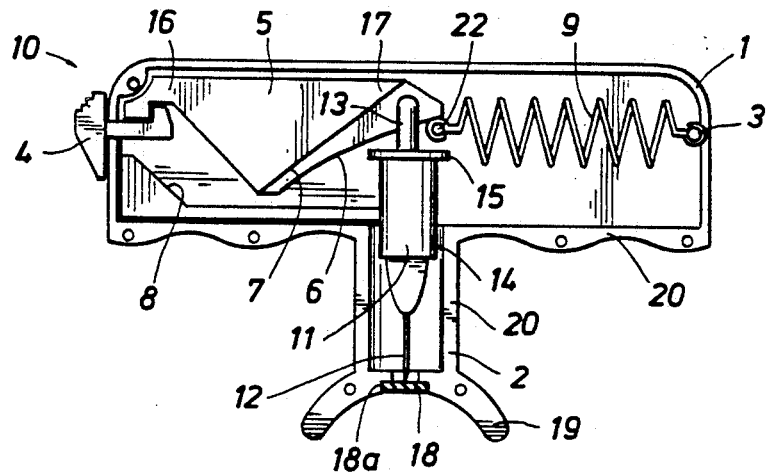
FIGS. 1A and 1B are sectional views of an automatic injection device which utilizes a cam and spring mechanism to move a needle between retracted and extended positions.
Figure 1B:
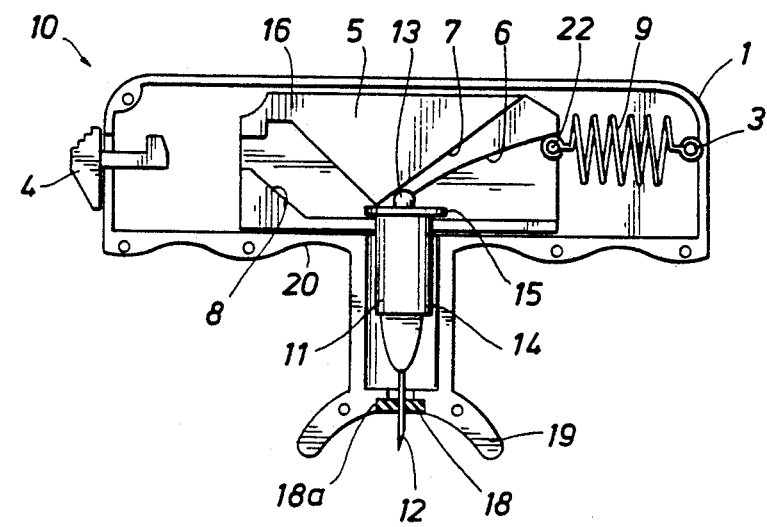

FIGS. 1A and 1B show one embodiment of an automatic injection device 10 which is formed of five major components: (1) a housing 20 with an elongated section 1 and a barrel section 2; (2) a sliding cam mechanism 5; (3) a trigger mechanism 4; (4) a spring 9; and (5) a syringe 11 which includes a needle 12 and a plunger 13. In general, the sliding cam mechanism 5 is slidably mounted within the elongated section 1 of the housing 20 and is powered by a spring 9. When the trigger mechanism 4 is actuated by the user as described below, the spring 9 moves the cam mechanism 5 from a first, loaded position to a second, unloaded position and in the process pushes the needle 12 to where it projects from the barrel section 2 (see FIG. 2), compresses the syringe plunger 13 to dispense a drug in the syringe, and retracts the needle 12 back into the housing 20.

The barrel section 2 of the housing 20 is formed integral with and perpendicular to the elongated section 1. The elongated section 1 is hollow and is sized and designed so the sliding cam mechanism 5 can slide from a first, loaded position adjacent the trigger mechanism 4 to a second, unloaded position at the other end of the elongated section 1. The housing 20 may be constructed of any suitable material, such as plastic or metal.

In one embodiment, the end of the barrel section 2 has curved section 19 to mate with an individual's penis during self-injection. This shape can be changed to correspond to any other anatomical shape depending on the shape of the injection site.

A seal 18, mounted in a snap ring 18a, is placed in the outer opening of the barrel section 2 for sealing the opening and preventing foreign objects from entering the housing 20. The seal 18 can be formed of any suitable penetrable material that can be sterilized such as neoprene rubber and is penetrated by the needle 12 when it moves to inject the drug.

The syringe 11 and the needle 12 can be provided as a component of the automatic injection device 10, as shown, where the device is used once and then discarded. However, the automatic injection device 10 could be provided without the syringe 11 and the needle 12, which could be inserted prior to use after the cam mechanism 5 is loaded. In this embodiment, the device 10 would be reusable, not disposable.

The syringe 11 may be any type of syringe commonly used in the medical industry or specifically designed. The syringe 11 has a barrel 14, a plunger 13, and a needle 12. If the needle 12 is to be used for the injection of a drug into the penis, the needle 12 can be a 25 to 30 gauge needle, designed for approximately 0.25 inch penetration.

The cam mechanism 5 is activated by the trigger mechanism 4. The cam mechanism 5 has a trigger engaging end 16 and a drive end 17. The trigger end 16 is detachably engaged to the trigger mechanism 4. The spring 9 is connected between the housing 20 through a suitable spring connection post 3 and to drive end 17 of the cam mechanism 5 through a spring connection post 22.

When the cam mechanism 5 is loaded as shown in FIG. 1A, the spring 9 is in tension. When the trigger mechanism 4 is pushed by the user to disengage it from the cam trigger end 16, the spring 9 operates to pull the sliding cam mechanism 5 toward to the unloaded position at the right side of the housing 20 as shown in FIGS. 1A and 1B.

The cam mechanism 5 has a first cam surface 6 which engages the top surface 15 of the syringe barrel 14 so that the syringe 11 with needle 12 is pushed to the extended position shown in FIG. 1B as the sliding cam mechanism 5 slides toward the unloaded position, i.e., the top surface 15 of the syringe barrel 14 follows the first cam surface 6. The cam mechanism 5 has a second cam surface 7 designed to interact with the syringe plunger 13 so that the syringe plunger 13 is compressed within the syringe 11 as the cam mechanism 5 slides toward the unloaded position, i.e., the syringe plunger 13 follows the second cam surface 7.

Thus, when the cam mechanism 5 moves from the loaded position to the unloaded position, the first cam surface 6 makes contact with the top surface 15 of the syringe barrel 14 and the second cam surface 7 makes contact with the syringe plunger 13, respectively pushing each toward the position shown in FIG. 1B. As the needle 12 moves downwardly it first penetrates the seal 18, then the skin and into the underlying tissue.

Figure 2:
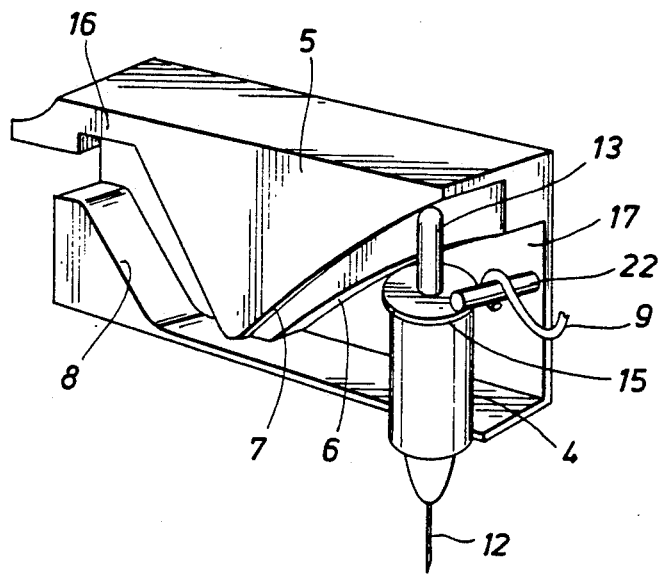
FIG. 2 is a perspective view of the pre-activation position of the syringe of FIG. 1A.

In the embodiment shown in FIGS. 1A, 1B and 2, the first and second cam surfaces 6, 7 are formed in a V-shape with the cam surface 6 (which engages the top surface 15 of the syringe) being formed at a smaller angle relative to the horizontal plane of movement than the cam surface 7 (which engages the plunger 13). This differential causes the syringe 11 to be moved downwardly by the cam surface 6 to where the needle 12 has penetrated the patient's skin before the cam surface 7 pushes the plunger 13 relative to the syringe to inject the drug.

With this shape of the first and second cam surfaces 6, 7, the syringe barrel 14 and syringe plunger 13 travel in sync with each other until the needle 12 has penetrated the skin to a depth of about 0.188 in. At this point the second cam surface 7 operates to push the syringe plunger 13 at a faster rate than the first cam surface 6 is pushing the syringe barrel 14, such that the syringe plunger 13 forces the drug contained in the syringe 11 through the needle 12 as the needle 12 continues to penetrate the tissue the remaining 0.125 in. of its travel to its final position at a penetration depth of about 0.25 in.

Retraction of the syringe 11 back into the housing 20 so the needle 12 is no longer exposed is accomplished by providing a third following cam surface 8 on the sliding cam mechanism 5 which contacts the top surface 15, which extends beyond the outer diameter of the syringe barrel 14, as the sliding cam mechanism 5 travels to the unloaded position. The extended top surface 15 follows the third cam surface 8, pulling the syringe barrel 14 and the needle 12 into a retracted position so it cannot accidentally puncture the skin of a handler.

Figure 3:
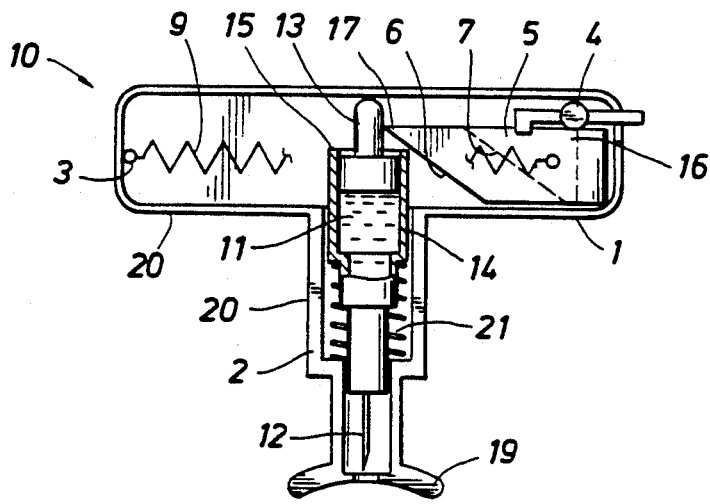
FIG. 3 is a schematic view of an alternate embodiment of the device where a spring is used for retracting the needle.
Figure 4:
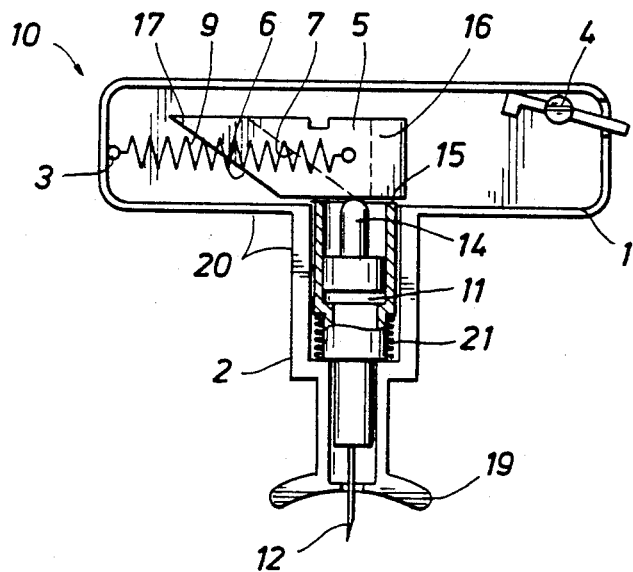
FIG. 4 is a schematic view of the device in FIG. 3 with the needle fully extended and the syringe plunger fully depressed.
Figure 5:
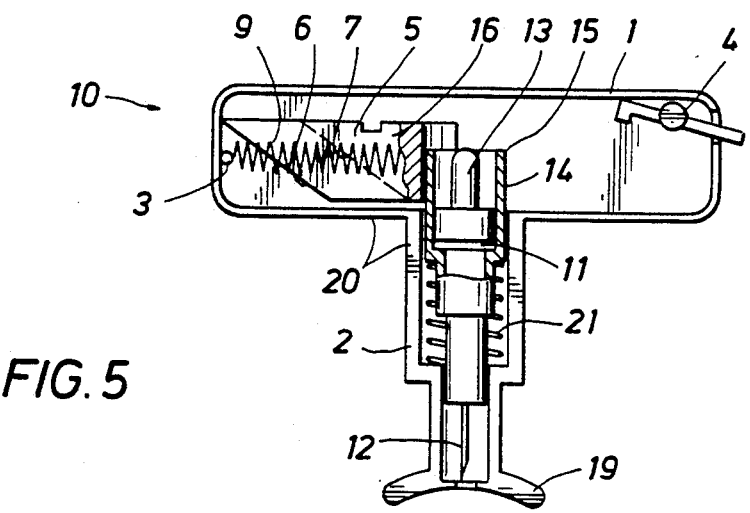
FIG. 5 is a schematic view of the device in FIG. 3 with the needle in a retracted position.

A second embodiment of the present invention is shown in FIGS. 3, 4 and 5, where a spring 21 is used to retract the syringe barrel 14 and the needle 12. The cam mechanism 5 is in the shape of a trapezoid (because the following cam surface 8 shown in FIGS. 1A, 1B has been eliminated). As the cam surfaces 6, 7 operate respectively to move the syringe barrel 14 and the needle 12 toward the extended position shown in FIG. 4, the syringe barrel 14 operates to compress the spring 21.

After the syringe 11 is fully extended and the syringe plunger 13 depressed, the sliding cam mechanism 5 is located in the position shown in FIG. 5 where it is no longer in contact with the syringe 11. The retraction spring 21 is then free to return to its uncompressed position, operating to automatically retract the syringe 11 with needle 12 into the barrel section 2.

The automatic injection device solves the problems mentioned above by providing a compact, discrete device which allows easy and accurate automatic self-injection of medication without the apprehension of viewing the needle. When the drug has been injected, the needle is automatically retracted into the housing 20 so that the possibility of an accidental puncture with the needle is eliminated.

Having described the invention above, various modifications of the techniques, procedures, material and equipment will be apparent to those skilled in the art. It is intended that all such variations within the scope and spirit of the invention be included within the scope of the appended claims.

What is claimed is:

1. An apparatus for injecting a medicament, comprising:
   (a) a housing;
   (b) a syringe having a syringe barrel for holding a medicament, a plunger movable within the barrel for ejecting the medicament from the barrel, and a hollow needle communicating with the barrel for transporting the medicament from the barrel to a patient;
   (c) mounting means for mounting the syringe in the housing and enabling the syringe to move from a first retracted position to a second extended position for injecting the medicament;
   (d) movement and injection means for moving the syringe from the first to the second position and pushing the plunger for injecting the medicament after the syringe has moved at least toward the second position;
   (e) retracting means for moving the syringe back to the first retracted position after the medicament has been injected
   wherein the housing has a first portion for holding the syringe and a second portion, perpendicular to the first portion, for holding the movement and injection means.

2. The apparatus of claim 1, wherein the syringe barrel has an upper surface and the plunger projects from the upper surface and wherein the movement and injection means comprises a cam with a first surface and a second surface for respectively engaging the upper surface and the plunger.

3. The apparatus of claim 2, wherein the movement and injection means further comprises a spring connected to the cam for moving the cam.

4. The apparatus of claim 2, wherein the upper surface has a rim projecting beyond the outer surface of the syringe barrel and the cam has a follower surface for engaging the rim for retracting the syringe into the housing.

5. The apparatus of claim 1, wherein the retracting means comprises a spring located in the first portion of the housing for retracting the syringe into the housing.

6. The apparatus of claim 1, wherein the first portion of the housing has an opening sealed with material capable of being penetrated by the needle.

7. The apparatus of claim 1, wherein the retracting means fully retracts the needle into the first portion of the housing.

8. An injection device for injection of fluid, comprising:
   a housing having an elongated section and a barrel section, said elongated section elongated in the direction of an axis, the barrel section integral with the elongated section and perpendicular to the axis, a spring attachment connection at an end of said housing along the axis, and a trigger mechanism at an opposite end of said housing along the axis;
   a sliding cam mechanism slidably mounted within said housing to slide in the direction of the axis, having a first cam surface, a second cam surface, a third cam surface, a drive end, and a trigger end, said trigger end designed to detachably engage said trigger mechanism; and
   a spring having a first end and a second end, the first end fixedly attached to said spring attachment connection, the second end fixedly connected to the drive end of the sliding cam mechanism.

9. The injection device of claim 8, further comprising: a syringe with needle, slidably located within said barrel section, said syringe having a syringe barrel and a syringe plunger, said syringe barrel having a top surface, said top surface located adjacent to the first cam surface so as to follow the first cam surface and located so as to contact the third cam surface and follow the third cam surface, said syringe plunger located adjacent to the second cam surface so as to follow the second cam surface.

10. The injection device of claim 8, wherein the injection device is for injection of liquid into a penis.

11. The injection device of claim 10, wherein the barrel section has a curved end section for mating with a penis.

12. The injection device of claim 11, wherein the needle is designed for a predetermined depth of penetration into the penis.

13. The injection device of claim 12, wherein the needle is an approximately 25 to 30 gauge needle, designed for approximately 0.25 inch penetration into the penis.

14. The injection device of claim 9, wherein the injection device is for injection of liquid into a penis.

15. The injection device of claim 14, wherein the barrel section has a curved end section for mating with a penis.

16. The injection device of claim 15, wherein the needle is designed for a predetermined depth of penetration into the penis.

17. The injection device of claim 16, wherein the needle is an approximately 25 to 30 gauge needle, designed for approximately 0.25 inch penetration into the penis.

18. An injection device for injection of fluid, comprising:
   a housing having an elongated section and a barrel section, said elongated section elongated in the direction of an axis, the barrel section integral with the elongated section and perpendicular to the axis, a spring attachment connection at an end of said housing along the axis, and a trigger mechanism at an opposite end of said housing along the axis;
   a sliding cam mechanism slidably mounted within said housing to slide in the direction of the axis, having a first cam surface, a second cam surface, a drive end, and a trigger end, said trigger end designed to detachably engage said trigger mechanism; and
   a spring having a first end and a second end, the first end fixedly attached to said spring attachment connection, the second end fixedly connected to the drive end of the sliding cam mechanism.

19. The injection device of claim 18, further comprising:
   a syringe with needle, slidable located within said barrel section, said syringe having a syringe barrel and a syringe plunger, said syringe barrel having a top surface, said top surface located adjacent to the first cam surface so as to follow the first cam surface, said syringe plunger located adjacent to the second cam surface so as to follow the second cam surface; and
   a retraction spring located within the barrel section so as to push the syringe with needle to a retracted position.

20. The injection device of claim 18, wherein the injection device is for injection of liquid into a penis.

21. The injection device of claim 20, wherein the barrel section has a curved end section for mating with a penis.

22. The injection device of claim 21, wherein the needle is designed for a predetermined depth of penetration into the penis.

23. The injection device of claim 22, wherein the needle is an approximately 25 to 30 gauge needle, designed for approximately 0.25 inch penetration into the penis.

24. The injection device of claim 19, wherein the injection device is for injection of liquid into a penis.

25. The injection device of claim 24, wherein the barrel section has a curved end section for mating with a penis.

26. The injection device of claim 25, wherein the needle is designed for a predetermined depth of penetration into the penis.

27. The injection device of claim 26, wherein the needle is an approximately 25 to 30 gauge needle, designed for approximately 0.25 inch penetration into the penis.

* * * * *